United States Patent [19]

Hsieh et al.

[11] Patent Number: 5,473,656

[45] Date of Patent: Dec. 5, 1995

[54] COMPUTED TOMOGRAPHY SYSTEM WITH CORRECTION FOR Z-AXIS DETECTOR NON-UNIFORMITY

[75] Inventors: Jiang Hsieh, Waukesha; Dale R. Thayer, New Berlin, both of Wis.

[73] Assignee: General Electric Company, Milwaukee, Wis.

[21] Appl. No.: 306,569

[22] Filed: Sep. 15, 1994

[51] Int. Cl.$^6$ ............................. A61B 6/03; G01N 23/083
[52] U.S. Cl. ................................ 378/4; 378/901; 378/15
[58] Field of Search ....................... 378/4, 14, 15, 378/19, 901

[56] References Cited

U.S. PATENT DOCUMENTS

| | | | |
|---|---|---|---|
| 4,035,651 | 7/1977 | LeMay | 378/9 |
| 4,991,189 | 2/1991 | Boomgaarden et al. | 378/4 |
| 5,131,021 | 7/1992 | Gard et al. | 378/19 |
| 5,224,136 | 6/1993 | Toth et al. | 378/4 |
| 5,301,108 | 4/1994 | Hsieh | 364/413.19 |
| 5,416,815 | 5/1995 | Hsieh | 378/4 |

Primary Examiner—David P. Porta
Assistant Examiner—David Vernen Bruce
Attorney, Agent, or Firm—Quarles & Brady

[57] ABSTRACT

An x-ray CT scanner acquires projection profiles $\overline{P}$ during a scan which are corrected for errors caused by non-uniform response of the detectors along the z-axis. In addition to corrections using a calibration vector Q that offsets errors caused by variations in the detector response, additional corrections are made to offset object dependent errors caused by the same variations in detector response when imaging certain objects.

8 Claims, 4 Drawing Sheets

FIG. 1(a)  FIG. (b)

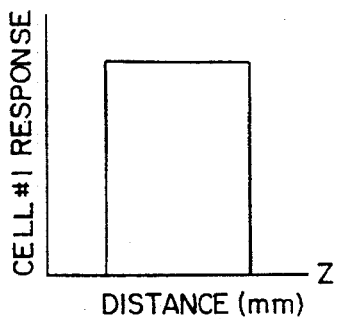
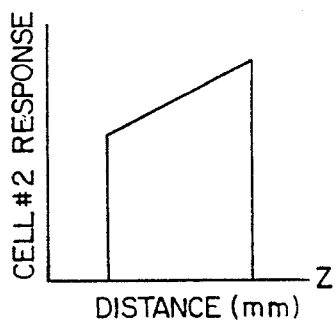
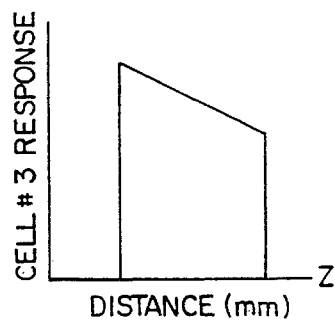
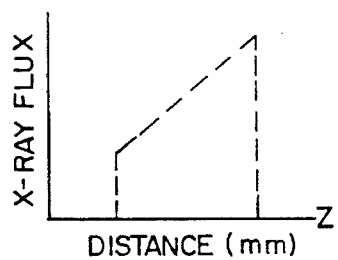
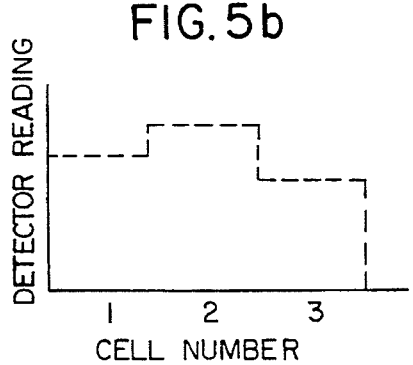
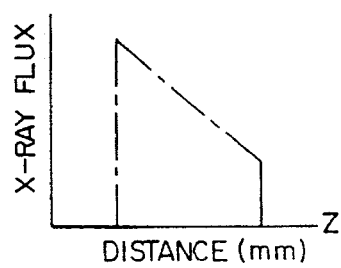
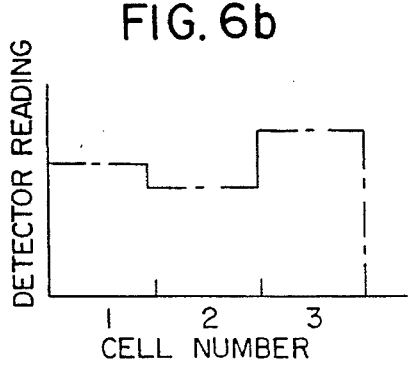

COMPUTED TOMOGRAPHY SYSTEM WITH CORRECTION FOR Z-AXIS DETECTOR NON-UNIFORMITY

BACKGROUND OF THE INVENTION

This invention relates to computed tomography equipment and specifically to the correction of errors caused by variations in x-ray detector sensitivity along the z-axis.

Computed tomography (CT) systems, include an x-ray source collimated to form a fan beam, the fan beam extending generally along a fan beam plane and directed through an object to be imaged. After passing through the imaged object, the fan beam is received by an x-ray detector array extending along the fan beam plane. The x-ray source and detector array are rotated together on a gantry within an imaging plane, generally parallel to the fan beam plane, around the image object.

The axis of rotation of the gantry is designated as the z-axis of the Cartesian coordinate system and the fan beam plane and imaging plane is parallel to the x-y plane of the coordinate system.

The detector array is comprised of detector cells each of which measures the intensity of transmitted radiation along a ray from the x-ray source to that particular detector cell. At each gantry angle, a projection is acquired comprised of intensity signals from each of the detector cells. The gantry is then rotated to a new gantry angle and the process is repeated to collect a number of projections along a number of gantry angles to form a tomographic projection set.

Each tomographic projection set is stored in numerical form for later computer processing to "reconstruct" a cross sectional image according to algorithms known in the art. The reconstructed image may be displayed on a conventional CRT or may be converted to a film record by means of a computer driven camera.

Ideally, the fan beam plane will strike the center line of the detector array. In practice, however, the fan beam plane may be displaced along the z-axis from the center line because of two effects. The first effect is the thermal expansion of the x-ray tube's anode and its support. The surface temperature of the tube's anode may rise as high as 2,000° C. and the anode supporting structure may rise to 400° C. or more. This heating and the resulting expansion of the tube's anode and its support causes a shifting of the focal spot of the tube which moves the point from which the x-rays emanate. The shifting of the focal spot causes a corresponding shift in the fan beam plane.

The second effect is the mechanical deflection of the gantry and anode support as the gantry rotates. This deforming stress results from the changing angle of gravitational acceleration and the changing magnitude of centripetal acceleration as a function of the rotational velocity of the gantry, acting both on the gantry and anode.

Displacement of the fan beam plane along the z-axis of the detector array is a problem because it causes variations in detector signals that are "exogenous" or unrelated to the internal structure of the imaged object. Generally each detector cell's sensitivity to x-rays will be a function of the z-axis position of the fan beam along the surface of that cell, that is, the detector cells exhibit a non-uniform "z-axis sensitivity". This z-axis sensitivity, combined with motion of the fan beam plane on the detectors, produces the undesired variations in the strength of the detector signal. Such exogenous variations in the detector signals produce undesirable ring like artifacts in the reconstructed image.

Displacement of the fan beam plane and thus variations in the detector signals may be predicted and corrected. In U.S. Pat. No. 4,991,189, issued Feb. 5, 1991, assigned to the same assignee as the present invention, and incorporated by reference, a control system using a movable collimator adjusts the z-axis position of the fan beam plane as deduced from a pair of special detector cells. The special detector cells provide information to a computer model of the system which in turn is used to control the collimator and to correct the placement of the fan beam plane. While such closed loop controls of the fan beam location reduce z-axis artifacts, they do not eliminate the problem.

Intercell sensitivity can be corrected using data from a calibration scan performed before a patient is in place. However, such corrections do not eliminate ring and band artifacts due to variations in detector sensitivity along the z-axis. Consider, for example, the z-axis sensitivity profiles of three different detector cells #1-3 in FIGS. 4(a)-4(c). Detector cell #1 represents a perfect sensitivity profile, while detector cells #2 and #3 represent actual sensitivity profiles with different characteristics. If these three detector cells are exposed to an x-ray flux which is uniform, the detector responses will differ because of the different z-axis sensitivities profiles, but these can be corrected using the calibration data.

Consider, however, the situation in which the x-ray flux is not uniform along the z-axis, but is instead variably attenuated by the patient being imaged. One such x-ray flux density profile is shown in FIG. 5(a), and the resulting response of these three detector cells after air calibration in FIG. 4 are shown in FIG. 5(b). On the other hand, consider a different x-ray flux density profile as shown in FIG. 6(a) and the resulting response of the same three detector cells after air calibration in FIG. 6(b). It is apparent that the corrections needed to level the detector responses is a function of the x-ray flux density profile, which in turn is a function of the attenuation characteristics of the object being imaged. In other words, the corrections needed depend on the object being imaged, and calibration data acquired with no object present will not suffice to eliminate ring and band artifacts caused by variations in the z-axis sensitivity of detector cells.

The problem is partially solved by acquiring calibration data using a phantom that simulates a subject that imposes a sloped x-ray flux density profile. Such a method is disclosed in U.S. Pat. No. 5,301,108 assigned to the same assignee as the present application and entitled "Computed Tomography System With Z-axis Correction".

SUMMARY OF THE INVENTION

The present invention relates to a method for correcting projection profile data for errors caused by variations in the z-axis sensitivity of detector elements and z-axis x-ray flux gradients produced by the patient being scanned. More specifically, the invention includes the acquisition of x-ray attenuation data, during a calibration scan and calculating a calibration vector $\overline{Q}$ which indicates corrections to be made to the attenuation signals as a function of the location of the fan beam along the z-axis; acquiring a projection profile $\overline{P}$ and correcting it using the calibration vector $\overline{Q}$ and the measured position of the fan beam along the z-axis; calculating an error vector $\overline{E}$ from the projection profile $\overline{P}$ indicative of the errors therein caused by non-uniform response of detector elements along the z-axis; calculating an offset value $\Delta Z$ from the error vector $\overline{E}$ and the calibration vector $\overline{Q}$; and further correcting the projection profile based on the offset value $\Delta Z$ and the calibration vector $\overline{Q}$.

A general object of the invention is to correct z-axis sensitivity errors which are introduced into the acquired x-ray attenuation profile when the structures through which the x-ray beam travels introduces a z-axis gradient in the x-ray flux density. Such object dependent errors cannot be corrected using conventional calibration techniques in which correction values are determined directly from a reference scan through air or a conventional phantom.

It has been discovered that object dependent errors can be reduced by adjusting the corrections made using beam z-axis position. This correction is an offset $\Delta Z$ to the measured fan beam position Z which is calculated using an error vector $\overline{E}$ derived from the projection profile $\overline{P}$.

A more specific object of the invention is to correct for data-dependant errors as the projection data is being acquired. Each projection profile can be examined, and if required, corrected prior to its use in reconstructing an image. The resulting increase in reconstruction time is not significant and no further processing is required after image reconstruction.

BRIEF DESCRIPTION OF THE DRAWINGS

FIGS. 4(a)–4(c) are graphic representations of three different z-axis sensitivity profiles of detectors used in the system of FIG. 1(a);

FIG. 5(a) is an exemplary x-ray flux density profile;

FIG. 5(b) is the resulting signals after air calibration produced by the detectors of FIGS. 4(a)–4(c);

FIG. 6(a) is a second exemplary x-ray flux density profile;

FIG. 6(b) is the resulting signals after air calibration produced by the detectors of FIGS. 4(a)–4(c)

DESCRIPTION OF THE PREFERRED EMBODIMENT

Figure 1:
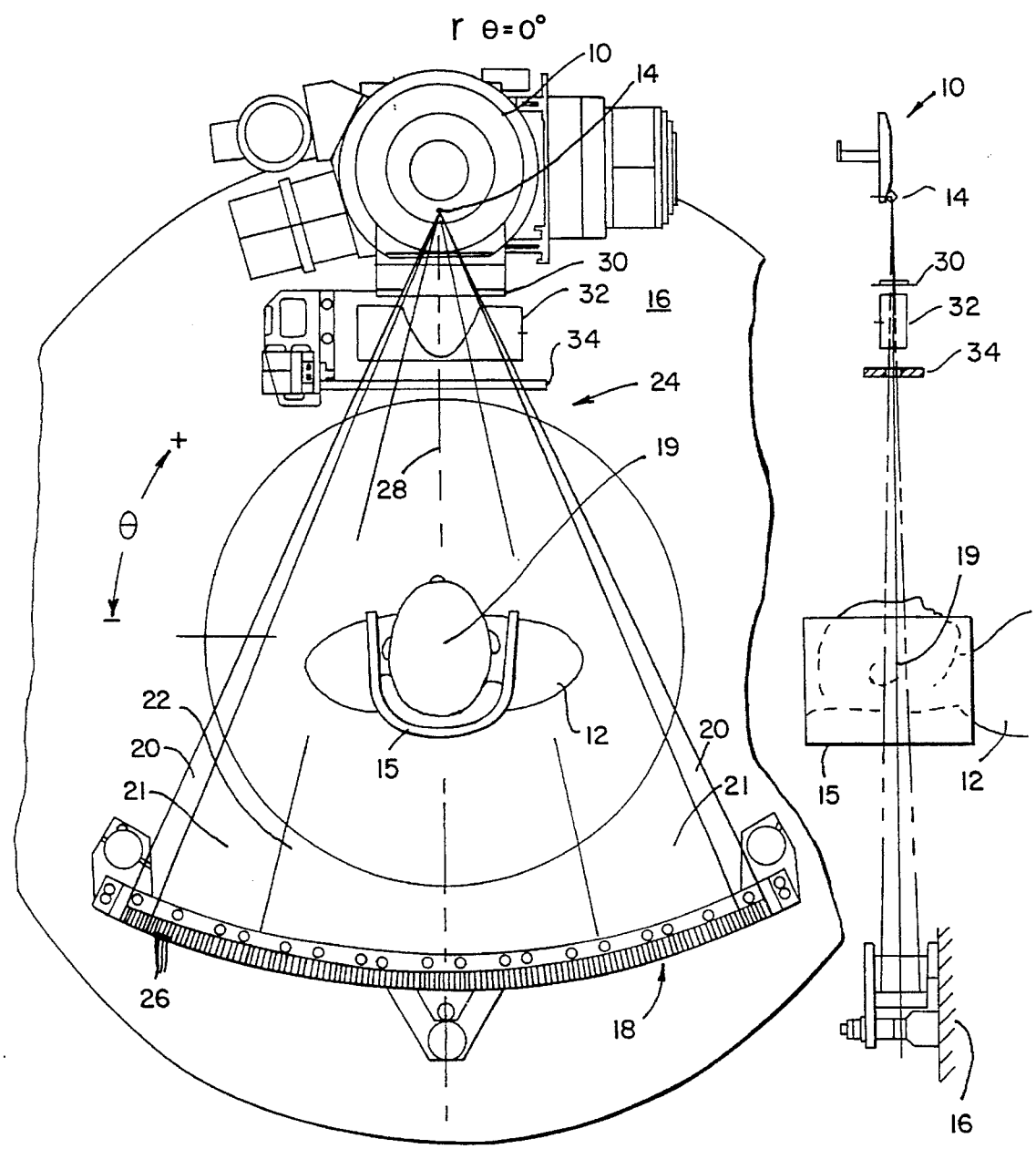
FIGS. 1(a)–1(b) are front and side views, in elevation, of a CT gantry showing the relative positions of an x-ray source, detector array an fan beam about a patient's head.

Referring to FIG. 1, a CT gantry 16, representative of that used with a "third generation" CT scanner, holds an x-ray source 10 producing a fan beam of x-ray 24. The fan beam 24 is directed through a patient 12, positioned near a center 19 of the gantry 16, to be received by a detector array 18 also attached to the gantry 16. The patient's head is supported by a headholder 15.

The gantry 16 rotates within an x-y plane of a Cartesian coordinate system, termed the imaging plane, which is generally the same plane as that of the fan beam 24.

The detector array 18 is comprised of a number of detector elements or "channels" 26 positioned adjacent to each other within the imaging plane to subtend the fan beam 24. The channels 26 receive and detect radiation passing from the x-ray source 10, to produce a plurality of channel signals each associated with a particular channel 26. At a given orientation of gantry 16 about patient 12, signals for approximately 800 channels may be acquired, representing a detailed picture of the line integral of the attenuation of the fan beam 24 by the patient 12 at that angle. A gantry angle of zero is defined as that angle where a principle ray 28, centered in the fan beam 24, is directed vertically downward from the x-ray source 10.

The x-rays of the fan beam 24, immediately after leaving x-ray source 10 and prior to being received by the detector array 18, are filtered by a spectral filter 30 which filters out the lower energy x-rays from the fan beam 24. The fan beam 24 then passes through a bow tie filter 32 having a profile that produces an attenuation in the fan beam 24 complementing that which would be produced by a cylinder of water placed at the center 19 of the gantry 16. The purpose of the bow tie filter 32 is to reduce the range of intensity values received by the detector channels 26 for a typical patient 12 and hence to allow for an increase in sensitivity of the detector array 18 and its associated circuitry.

The bow tie filter 32 is followed by an aperture 34 which forms fan beam 24 and may be used to correct the position of the fan beam 24 with respect to the surface of the detector array 18 as described generally in U.S. Pat. 5,054,041 issued to the same assignee as that of the present application and incorporated herein by reference.

For a given patient 12, the channels 26 may be roughly divided into three groups: reference, overrange, and in-range. Reference channels 20 of the detector array 18 are those intended not to be occluded by the patient 12 or headholder 15 and may serve the function of calibrating the projection data for variations in the x-ray flux from x-ray source 10, and serve further to permit automatic alignment of the fan beam 24 on the detector array 18. Over-range channels 21 of the detector array 18 are those channels within a given projection which, although possibly occluded by the imaged object 12, generally receive x-rays having so little attenuation that the ADC, used to digitize the signals of these channels, is over-ranged. And finally, in-range channels 22 of the detector array 18, are those in a given projection which are sufficiently attenuated by the imaged object 12 so as not to overrange the ADC used to digitize the signals from these channels.

Figure 2:
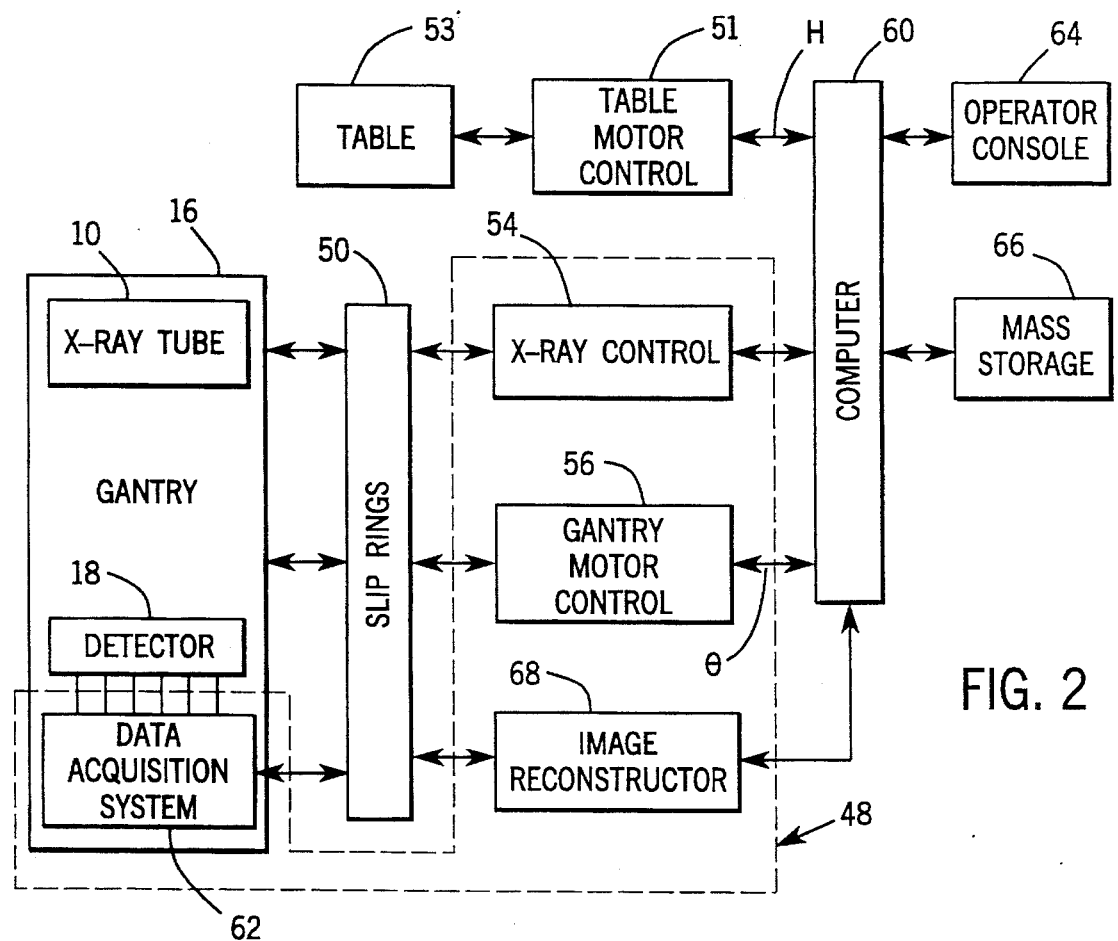
FIG. 2 is a block diagram of a CT control system associated with the gantry of FIG. 1 and useful for practicing the present invention.

Referring to FIG. 2, control circuitry for a CT imaging system suitable for use with the present invention includes a number of functional blocks 48. A data acquisition system 62 is connected to the detector array 18 and comprises a sampling means (not shown) for sampling the signals from each of the channels 26. An analog to digital converter ("ADC") (not shown) converts the sampled analog signals from each sampled channel 26 to a digital value for processing by later circuitry.

A radiotranslucent table 53 supports the patient 12 and the headholder 15, the latter which is typically fixed to the table 53. The table 53 may be moved through the image plane to align the slice of interest of the patient with the image plane, and may be raised or lowered to center the patient 12 within the opening of the gantry 16. The movement of the table is accomplished by motors (not shown) controlled by table motor control 51. The table motor control 51 also generates a value H indicating the height of table 53 with respect to the isocenter 19.

An x-ray control 54 provides power and timing signals to the x-ray source 10 with regard to the position of gantry 16 to acquire the projections. Gantry motor controller 56 controls the rotational speed and position of the gantry 16 and provides gantry angle information θ to the DAS 62 and the x-ray control 54 to permit accurate timing of the projections.

The image reconstructor 68 is a special purpose computer, such as an array processor, capable of very rapid parallel processing or "pipelining" as is necessary to produce images from the large amount of projection data. Array processors suitable for use as the image reconstructor 68 are commercially available from a variety of sources. The image reconstructor 68 receives the sampled and digitized signals from the channels 26 of the detector array 18 via the DAS 62 to perform high speed image reconstruction according to methods known in the art.

A computer 60 coordinates the operation of the DAS 62, the table motor control 51, the x-ray control 54, and the gantry motor control 56 and works in conjunction with image reconstructor 68 to reconstruct tomographic images from the set of projections acquired by the scanning process. The computer 60 receives commands and scanning parameters via operator console 64 which is generally a CRT display and keyboard which allows the operator to enter parameters for the scan and to display the reconstructed slice images and other information from the computer 60. A mass storage device 66 provides a means for storing operating programs for the CT imaging system, as well as image data for future reference by the operator.

Each of the above elements is connected to its associated elements on the gantry 16 via slip rings 50 to permit continuous rotation of the gantry 16.

Before reconstructing an image with the acquired attenuation profile $\bar{P}$ a number of corrections are made to the sampled detector signals. One of these corrections is to adjust the detector signal to offset variations caused by changes in the location of the x-ray beam along the z-axis. To accomplish this, special detector cells described in the above-cited U.S. Pat. No. 4,991,189 provide feedback information indicating the location (z) of the x-ray beam along the z-axis. A corrected scan data profile $\bar{P}'$ is then calculated using the following equation:

$$\bar{P}' = \bar{P}\left(1 + \frac{Z - Z_{cold}}{Z_{cold}} \bar{Q}\right) \tag{1}$$

where Z is the present average position of the x-ray beam, $Z_{cold}$ is a reference beam position when the system is first started, and $\bar{Q}$ is a set of correction values for the respective detector elements. The correction values $\bar{Q}$ indicate the rate of change of detector signal output as a function of Z location, and they are determined during a calibration procedure. These detector deterioration "signatures" can be obtained in a number of ways in addition to that described in U.S. Pat. No. 4,991,189. For example, $\bar{Q}$ can be derived from the detector z-axis profiles directly.

It is a discovery of the present invention that the image artifacts caused by degraded detector response along the z-axis can be removed by appropriately adjusting the value of Z input to the correction equation (1). If we denote by $\Delta Z$ the amount that Z has to be modified to arrive at a z-axis artifact free image, the newly corrected scan data profile P" is:

$$\bar{P}'' = \bar{P}\left(1 + \frac{Z + \Delta Z - Z_{cold}}{Z_{cold}} \bar{Q}\right) \tag{2}$$

Considering the fact that minus logarithm is performed on the scan data profile and the fact that $\log(1+x) \approx x$ for $x \ll 1$, the above equation can be re-written as follows:

$$-\log(\bar{P}'') \approx -\log(\bar{P}) - \left(\frac{Z + \Delta Z - Z_{cold}}{Z_{cold}} \bar{Q}\right) \tag{3}$$

It then follows:

$$-\log(\bar{P}') + \log(\bar{P}'') \approx \frac{\Delta Z}{Z_{cold}} \bar{Q} \tag{4}$$

It can be seen that the term on the left hand side of equation (4) represents the error in the scan data projection due to x-ray degradation of the detectors. If this error, $\bar{E}$, can be calculated, the amount of changes required in the z-average value, $\Delta Z$, is then simply:

$$\Delta Z \approx \frac{\bar{E} \times Z_{cold}}{\bar{Q}} \tag{5}$$

Because some of the elements in $\bar{Q}$ can be zeroes, the value of $\Delta Z$ is obtained by a first order polynomial fit of $\bar{E} \times Z_{cold}$ with $\bar{Q}$ as an independent variable. This is a "least square" error solution to equation (5), but it should be apparent to those skilled in the art that other solutions which minimize overall errors are also possible. Note that $\Delta Z$ is simply the coefficient of the linear term in such a fit.

The error vector $\bar{E}$ can be obtained by a two stage high pass filtering of the projection data to arrive at the "errors" from each projection. This two stage filtering can be combined into a single high pass filter if desired, or it can be further separated into multiple stages. Also, because equation (4) also applies to the scan data before the—logarithm is calculated, the error $\bar{E}$ can also be estimated using this scan data. The errors are then averaged over all views or a portion of all views in the scan to improve the statistics of the estimation and to reduce the dependency on object location. To improve the sensitivity of the estimation, the error vector $\bar{E}$ is based on the central 30 detector channels, although this may be a configurable parameter.

For head scans, the slope in the z-direction occupies the entire image. Therefore, error calculations performed on the center 30 channels will be a true representation of the errors for the entire object, and the resulting $\Delta Z$ can be applied to the entire projection. For body scans, however, this condition is no longer valid. A typical sloped object in a body (top of the liver or bottom of the heart) occupies only a small portion of the entire image. The error estimated on the center channels will not be an accurate estimation of errors for outer channels. Therefore, it is desirable to have the flexibility of turning off the correction on the outer channels when a body scan is performed. This can be easily accomplished by rewriting equation (2) in the following form:

$$\bar{P}'' = \bar{P}\left[\left(1 + \frac{Z - Z_{cold}}{Z_{cold}} \bar{Q}\right) + \frac{\Delta Z}{Z_{cold}} \bar{Q}\right] \tag{6}$$

The second term inside the brackets corresponds to the conventional z-axis correction to be applied to the entire profile. If a window function $\Omega$ is applied to the second term to limit its domain, the z-axis correction according to the present invention can then be easily controlled within the desired FOV. The window function $\Omega$ is a smooth function which avoids abrupt changes. The final correction is then simply:

$$\bar{P}'' = \bar{P}\left[\left(1 + \frac{Z - Z_{cold}}{Z_{cold}}\bar{Q}\right) + \frac{\Delta Z}{Z_{cold}}\bar{Q}\Omega\right] \quad (7)$$

It is important that the correction not introduce additional error when $\bar{E}$ and $\bar{Q}$ are dissimilar. This can be accomplished by calculating the "goodness of fit" during the $\Delta Z$ estimation process, since $\Delta Z$ is calculated based on the polynomial fit of $\bar{E} \times Z_{cold}$ with $\bar{Q}$ as an independent variable. An example of "goodness of fit" is the absolute value of the correlation coefficient between $\bar{E} \times Z_{cold}$ and $\bar{Q}$. When the correlation coefficient is high, it indicates that the estimated error is most probably caused by the z-axis degradation and the correction process should be applied. If, on the other hand, the correlation coefficient is low, the correction will most probably introduce new errors and should not be applied.

When a high contrast object (such as metal) is present in the center of the image, the filter used to calculate $\bar{E}$ cannot remove all the information related to the object because of its high frequency content. Therefore, the "error" $\bar{E}$ contains not only the signals related to the detector deterioration, but also the signals related to the high contrast object. Because of its high contrast nature, the signals are generally much larger than the true error signals, and a false error vector will be generated. This phenomenon is more pronounced for half scans since much of the false errors are cancelled out in a full scan. A more detailed analysis has shown that almost all of the problems occur at very high values of $\Delta Z$. A simple fix is to turn off the correction for all cases where $\Delta Z$ is larger than a predetermined threshold. Although this solution is simple to implement, it was found that many scans with a high $\Delta Z$ benefit from the correction.

Figure 7:
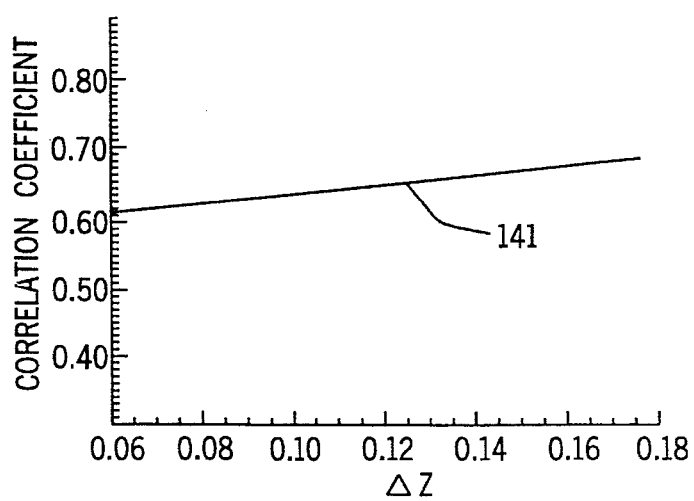
FIG. 7 is a graphic representation of a decision boundary used in the processing of FIG. 3.

The solution implemented in the preferred embodiment of the invention is to establish a correlation coefficient threshold based on the calculated value of $\Delta Z$. If the calculated correlation coefficient exceeds this threshold, the correction is made, otherwise, the correction is not made. Such a decision boundary is shown in FIG. 7 which may be stored as a table of values or as an equation.

Figure 3:
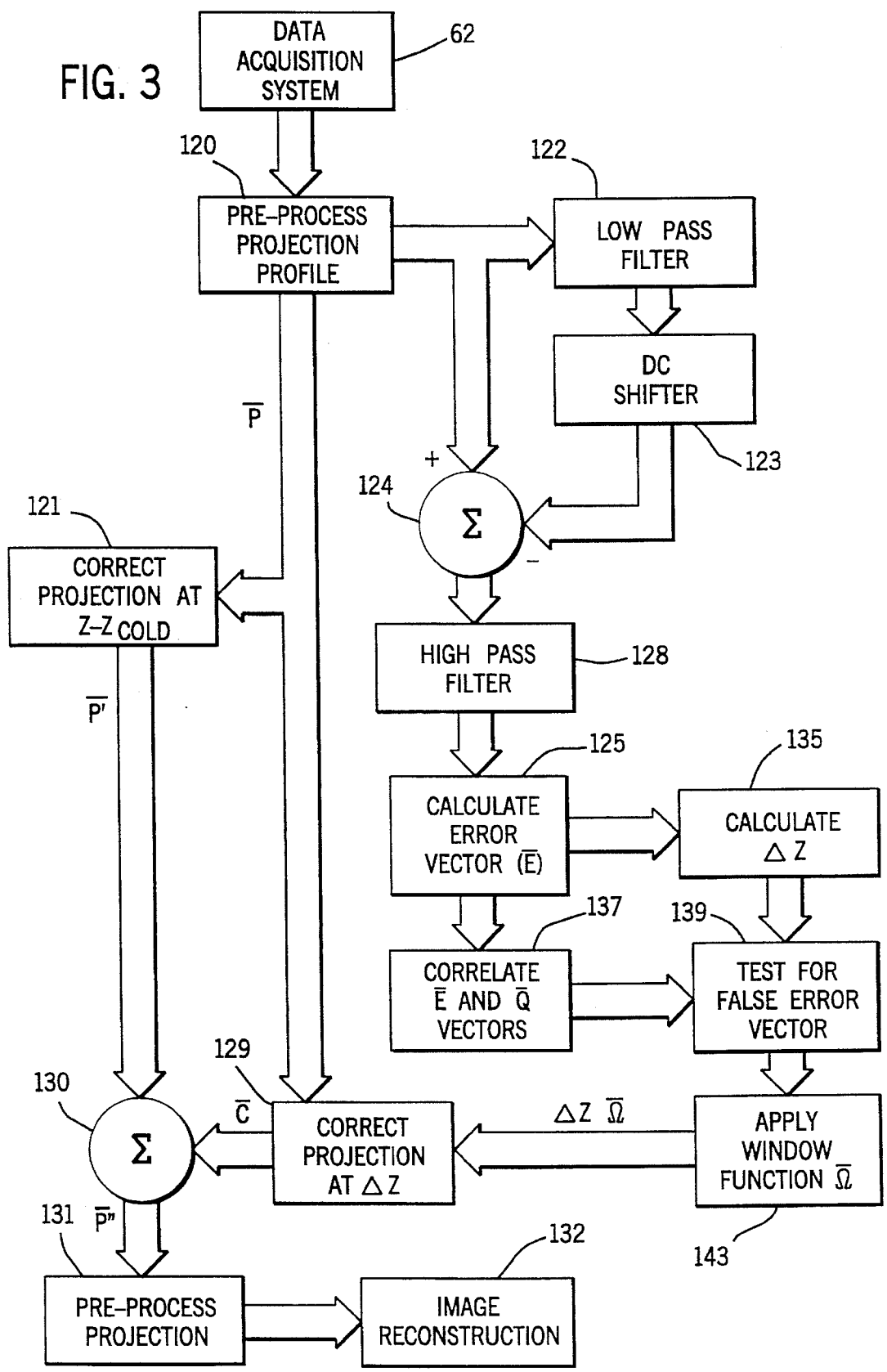
FIG. 3 is a block diagram showing the processing of the data acquired by the CT system of FIG. 2 according to the present invention.

Referring particularly to FIG. 3, the image reconstructor 68 is modified to correct the fully preprocessed projection profiles as they are received at memory block 120 from the data acquisition system 62. Each projection profile ($\bar{P}$) is one view which includes separate values for each of the 852 detector elements that have been preprocessed to compensate for differences in channel gain, detector offsets, etc. The pre-processed projection profile $\bar{P}$ is corrected as described above with respect to equation (1) at process block 121 using the $\bar{Q}$ vector created during calibration and the fan beam position Z received from the position detector. The present invention adds to this corrected projection $\bar{P}'$ further corrections calculated at process block 129 as will be described in detail below. These further corrections will be summed at 130 with corrected projection $\bar{P}'$ to produce the final projection $\bar{P}''$ defined above in equation (2) and final preprocessing steps such as beam hardening are then performed at process block 131. The fully preprocessed projection $\bar{P}''$ is then used to reconstruct the image at process block 132. Only the central 65 values in the projection profile $\bar{P}$ are used to calculate the corrections at process block 129 as will now be described.

Referring still to FIG. 3, the first task is to identify the error components in the projection profile $\bar{P}$ caused by detector z-axis degradation operating with an x-ray beam having a Z gradient. This is the error vector $\bar{E}$ discussed above with respect to equation (5). The first step is to separate variations in the projection data due to the structures that belong in the patient being scanned. This is accomplished by passing the central 65 channels through a low pass filter 122. The low pass filter is designed such that all the high frequency fluctuations due to z-axis errors are filtered out and the main structures of the object are preserved. A 13 point box car filter is used for this purpose. To avoid a DC shift in the filtered data, the entire projection is shifted at 123 by an amount so that the central 65 channels have the same average value as the central 65 channels of the unfiltered projection profile. The filtered output of the shifter 123 is then subtracted from the central 65 channels of the original projection data $\bar{P}$ at summing point 124 to produce a 65 element vector that is input to a high pass filter 128. The high pass filter 128 is implemented by passing a copy of the input vector through a 13 point low pass Gaussian filter and subtracting the result from the input vector. The resulting error candidate vector ($\bar{E}$) embodies the fluctuations in the central 65 channels of the projection profile data that are likely to be caused by non-uniform detector element z-axis response. This vector ($\bar{E}$) is averaged at 125 with the error candidate vectors for the previously processed projection profiles for this scan. This running average of the error vector ($\bar{E}$) is used in the subsequent calculations.

The z-axis modification $\Delta Z$ is calculated from the average error vector $\bar{E}$ and the stored $\bar{Q}$ vector as described above with respect to equation (5). This calculation is performed at process block 135 which makes a first order polynomial fit of $\bar{E} \times Z_{cold}$ to the $\bar{Q}$ vector as independent variable and $\Delta Z$ as its coefficient. In other words, $\Delta Z$ is found which minimizes the following quantity:

$$\Sigma(\bar{E} \times Z_{cold} - \Delta Z \bar{Q})^2. \quad (8)$$

While the calculated value $\Delta Z$ could be used directly to calculate the further corrections at process block 129, this is not done because of the risk of introducing errors. First, it has been discovered that when $\Delta Z$ is large, very often this is due to metal objects in the field of view, such as paper clips, bullet fragments, etc. The sharp variations in the projection profile $\bar{P}$ which such objects produce are not completely filtered out by the high pass filter 128, and $\Delta Z$ may be erroneously increased.

To test for this condition the average error vector $\bar{E}$ is cross correlated with the stored $\bar{Q}$ vector as indicated at process block 137. The resulting correlation coefficient indicates how well the $\bar{E}$ vector fits the $\bar{Q}$ vector and thus provides a good indication of the integrity of the error vector $\bar{E}$. The correlation coefficient and the calculated $\Delta Z$ are input to process block 139 where a test is conducted to decide if a valid error vector $\bar{E}$ was used to calculate $\Delta Z$. In the preferred embodiment a table of values which define the line 141 in FIG. 7 are stored. Using the calculated $\Delta Z$ as an index into this table a minimum correlation coefficient is read from the table and compared with the calculated correlation coefficient. If the minimum value is exceeded, the correction is made. The values in this table are determined empirically and may be changed when imaging different portions of the human anatomy. This table can also be extended to smaller values of $\Delta Z$ if desired.

Referring again to FIG. 3, if the correction is to be made, the $\Delta Z$ is combined with a window function $\bar{\Omega}$ at process block 143. As explained above in connection with equations (6) and (7), the window function $\bar{\Omega}$ enables the corrections to be limited in the FOV to those portions of the anatomy that are likely to produce z-axis errors. The particular window function used may be selected by the operator or it may be selected as part of an automatic configuration protocol for particular anatomies.

The final step in the process is to correct the projection profile $\bar{P}$ at process block 129 using the "windowed" $\Delta Z$ and the stored $\bar{Q}$ vector. This correction ($\bar{C}$) is the second term in the above described equation (7):

$$\bar{C} = \bar{P}(\Delta Z/Z_{cold})\bar{Q}\bar{\Omega} \qquad (9)$$

The correction $\bar{C}$ is combined with the corrected projection profile $\bar{P}'$ at summing point 130, and is used with the other similarly corrected views in the scan to reconstruct an image at 131.

There are many variations possible to the preferred embodiment described above without departing from the spirit of the invention. For example, if the window function $\Omega$ is not employed (e.g. when small objects are scanned), the value of $\Delta Z$ can be combined before the correction is made at process block 121. Also, the error vector $\bar{E}$ may be derived using the entire projection or only a central part of it, and the $\Delta Z$ may be either independent or dependent on the view angle at which the projection data is acquired.

We claim:

1. A method for correcting x-ray data for a computed tomography system having an x-ray source for producing a fan beam of x-rays along a fan beam plane and with a thickness along an axis normal to the fan beam plane, and having a set of detector elements disposed in the fan beam of x-rays to produce a corresponding set of attenuation signals that indicate the x-ray flux density profile of the fan beam, the steps comprising:

a) acquiring a set of attenuation signals from the detector elements during a calibration scan and calculating a calibration vector $\bar{Q}$ which indicates corrections to be made to the attenuation signals as a function of the location of the fan beam plane along said axis;

b) acquiring a set of attenuation signals from the detector elements during a scan of a subject and producing a projection profile $\bar{P}$;

c) correcting the projection profile $\bar{P}$ using the calibration vector $\bar{Q}$ and the measured position of the fan beam plane along said axis;

d) calculating an error vector $\bar{E}$ from the projection profile $\bar{P}$ indicative of the errors therein caused by nonuniform response of detector elements along said axis;

e) calculating an offset value $\Delta Z$ from the error vector $\bar{E}$ and the calibration vector $\bar{Q}$;

f) further correcting the projection profile $\bar{P}$ by calculating corrections $\bar{C}$ based on the offset value $\Delta Z$, the calibration vector $\bar{Q}$ and projection profile $\bar{P}$;

g) repeating steps b) through f) to perform a scan in which a plurality of corrected projection profiles are produced; and h) reconstructing an image using said plurality of corrected projection profiles.

2. The method as recited in claim 1 in which step d) is performed by filtering the projection profile $\bar{P}$; and averaging the filtered projection profiles $\bar{P}$ acquired during the scan.

3. The method as recited in claim 1 in which step e) is performed using the following relationships:

$$\Delta Z = \bar{E} \times Z_{cold}/\bar{Q}$$

where $Z_{cold}$ is the location of the fan beam plane along said axis when the computed tomography system is first operated.

4. The method as recited in claim 3 in which the offset value $\Delta Z$ is calculated by a first order polynomial fit of the product $\bar{E} \times Z_{cold}$ to the product $\Delta Z \times \bar{Q}$.

5. The method as recited in claim 1 which includes calculating the correlation of the error vector $\bar{E}$ and the calibration vector $\bar{Q}$ and inhibiting step f) if the resulting correlation coefficient does not exceed a predetermined amount.

6. The method as recited in claim 5 in which the predetermined amount changes as a function of the calculated offset value $\Delta Z$.

7. The method as recited in claim 1 in which the corrections $\bar{C}$ calculated in step f) are calculated according to the expression:

$$\bar{C} = \bar{P}(\Delta Z/Z_{cold})\bar{Q}$$

where $Z_{cold}$ is the location of the fan beam plane along said axis when the computed tomography system is first operated.

8. The method as recited in claim 1 in which the corrections $\bar{C}$ calculated in step f) are multiplied by a window function $\bar{\Omega}$ which limits the field of view over which the corrections are made.

* * * * *